United States Patent
Armstrong et al.

(10) Patent No.: US 9,629,204 B2
(45) Date of Patent: Apr. 18, 2017

(54) DETECTION AND CORRECTION OF WINDOW MOISTURE CONDENSATION

(71) Applicant: Teledyne Instruments, Inc., Thousand Oaks, CA (US)

(72) Inventors: Jason Armstrong, Lincoln, NE (US); Shannon Cushman, Lincoln, NE (US); Phillip B. Liescheski, Lincoln, NE (US); Paul Spieker, Pleasant Dale, NE (US)

(73) Assignee: Teledyne Instruments, Inc., Thousand Oaks, CA (US)

( * ) Notice: Subject to any disclaimer, the term of this patent is extended or adjusted under 35 U.S.C. 154(b) by 420 days.

(21) Appl. No.: 14/221,578

(22) Filed: Mar. 21, 2014

(65) Prior Publication Data

US 2016/0113067 A1    Apr. 21, 2016

(51) Int. Cl.
*H05B 1/00* (2006.01)
*H05B 3/84* (2006.01)
*G01N 21/15* (2006.01)

(52) U.S. Cl.
CPC .............. *H05B 3/84* (2013.01); *G01N 21/15* (2013.01); *G01N 2021/151* (2013.01); *G01N 2021/155* (2013.01); *G01N 2021/157* (2013.01); *G01N 2021/158* (2013.01)

(58) Field of Classification Search
CPC .......... H05B 3/84; H05B 3/86; H05B 1/0231; H05B 2203/035; G01N 21/15; G01N 2021/151; G01N 2021/157; G01N 2021/158; G01N 2021/155; B60H 1/00785
See application file for complete search history.

(56) References Cited

U.S. PATENT DOCUMENTS

| | | |
|---|---|---|
| 3,225,173 A | 12/1965 | Cook et al. |
| 3,868,492 A | 2/1975 | Taylor |
| 3,902,040 A | 8/1975 | Ikeda et al. |
| 4,196,338 A | 4/1980 | Edel |
| 4,260,876 A * | 4/1981 | Hochheiser ............ F25D 21/04 219/203 |
| 4,665,351 A | 5/1987 | Nyberg |
| 5,278,412 A | 1/1994 | Dethomas et al. |
| 5,313,072 A | 5/1994 | Vachss |
| 5,331,178 A | 7/1994 | Fukuda et al. |
| 5,464,982 A | 11/1995 | Drucker et al. |
| 5,493,190 A | 2/1996 | Mueller |
| 5,639,393 A | 6/1997 | Veltum et al. |
| 6,049,069 A * | 4/2000 | Hochstein .......... B60H 1/00785 219/203 |

(Continued)

FOREIGN PATENT DOCUMENTS

| | | |
|---|---|---|
| DE | 2361579 A1 | 6/1975 |
| EP | 1936358 A1 | 6/2008 |

(Continued)

*Primary Examiner* — Shawntina Fuqua
(74) *Attorney, Agent, or Firm* — Sulter Swantz pc llo

(57) ABSTRACT

Condensation mitigation devices and condensation prediction/detection techniques configured to prevent window condensation with reduced power consumption are disclosed. A condensation mitigation device is configured to predict and/or detect a window condensation event. The condensation mitigation device is powered on only during such an event, and the condensation mitigation device is powered off afterwards to conserve power.

25 Claims, 4 Drawing Sheets

(56) References Cited

U.S. PATENT DOCUMENTS

| | | |
|---|---|---|
| 6,191,421 B1 | 2/2001 | Yamamori et al. |
| 2002/0005941 A1 | 1/2002 | Kawaguchi et al. |
| 2003/0133185 A1 | 7/2003 | Dunn et al. |
| 2004/0094529 A1 | 5/2004 | Richter |
| 2004/0109174 A1 | 6/2004 | Lebel et al. |
| 2005/0145796 A1* | 7/2005 | Davis .................. A61B 5/083 250/343 |
| 2005/0285557 A1 | 12/2005 | Morishita |
| 2010/0013984 A1 | 1/2010 | Loiacono |
| 2013/0039810 A1 | 2/2013 | Riechers |
| 2013/0215411 A1 | 8/2013 | Christian et al. |

FOREIGN PATENT DOCUMENTS

| | | |
|---|---|---|
| GB | 1522965 A | 8/1978 |
| GB | 2408798 A | 6/2005 |
| JP | 2000227397 A | 8/2000 |
| JP | 2000296762 A | 10/2000 |

* cited by examiner

DETECTION AND CORRECTION OF WINDOW MOISTURE CONDENSATION

TECHNICAL FIELD

The disclosure generally relates to condensation removal, and particularly to systems and methods for detection and correction of window moisture condensation.

BACKGROUND

Condensation is the change of the physical state of matter from gas phase into liquid phase. Moisture condensation on a window is unfavorable and should be prevented or mitigated in certain environment.

SUMMARY

Accordingly, an embodiment of the present disclosure is directed to a condensation detection and mitigation apparatus for a window. The apparatus includes at least one condensation detection sensor configured for detecting a condensation condition, and a controller configured for conditionally activating a condensation mitigation device for the window based on the detection of the condensation condition.

A further embodiment of the present disclosure is directed to a condensation detection and mitigation method. The method includes: detecting a condensation condition on a window; activating a condensation mitigation device for the window based on the detection of the condensation condition; and deactivation the condensation mitigation device for the window based on at least one of: a detection of a deactivation condition; and a lapse of a predetermined period of time since the activation of the condensation mitigation device.

An additional embodiment of the present disclosure is directed to a system. The system includes a protective housing having a window and an optical device positioned inside the protective housing, wherein the optical device is configured for obtaining optical data through the window. The system also includes at least one condensation detection sensor configured for detecting a condensation condition, and a controller configured for conditionally activating a condensation mitigation device for the window based on the detection of the condensation condition.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous objects and advantages of the present disclosure may be better understood by those skilled in the art by reference to the accompanying figures in which.

DETAILED DESCRIPTION

Figure 1:
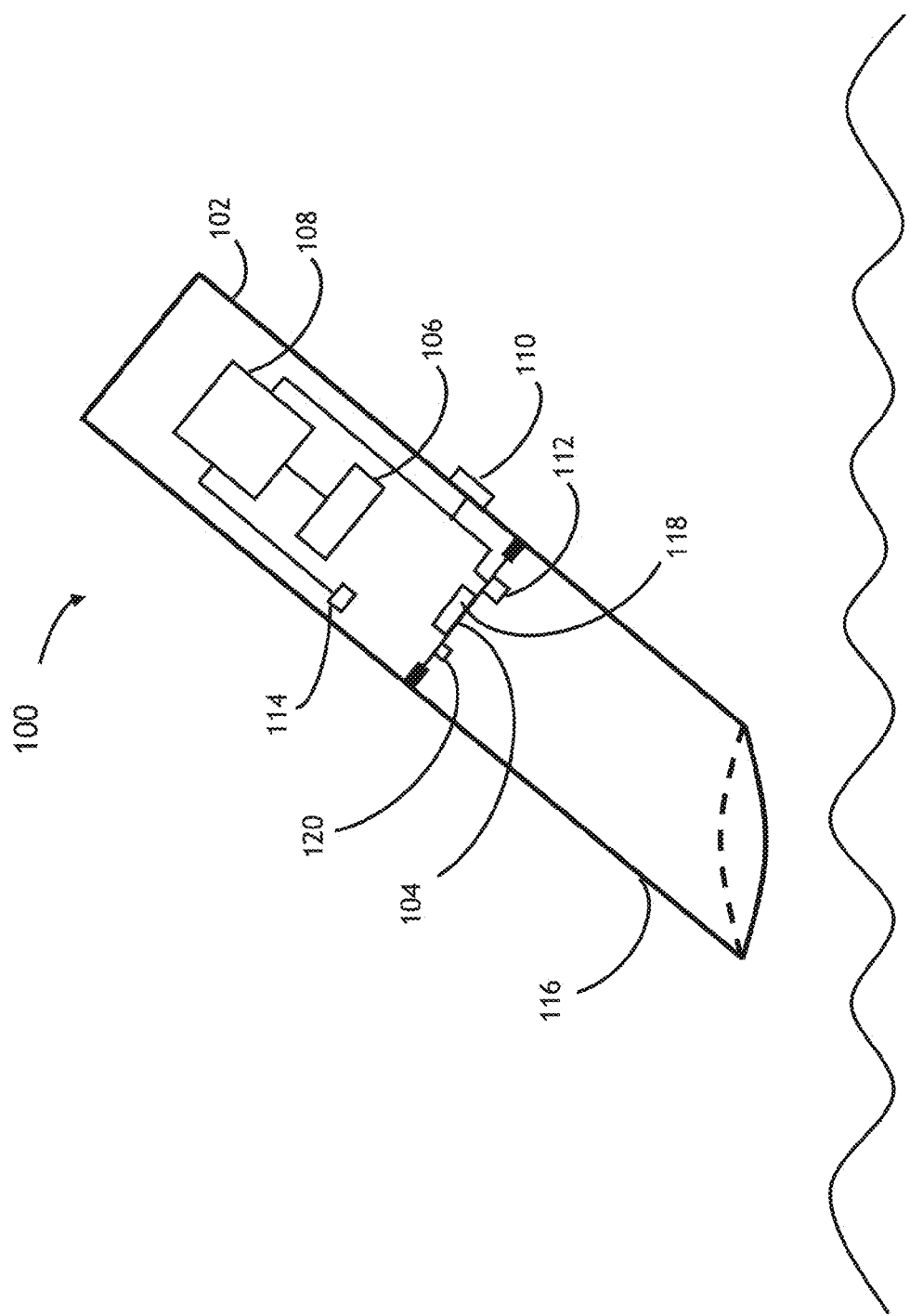
FIG. 1 is a block diagram depicting a system utilized for performing noncontact open channel fluid flow measurement.

Reference will now be made in detail to the subject matter disclosed, which is illustrated in the accompanying drawings.

Principles of the present invention will be described herein in the context of illustrative embodiments of detection and correction of window moisture condensation for instruments in corrosive and/or humid environments such as sewer environments. It is to be appreciated, however, that the embodiments of the present invention are not limited to the specific apparatus, methods and environments illustratively shown and described herein.

While illustrative embodiments of the invention will be described herein with reference to laser-based instruments, it is to be appreciated that the embodiments of the present invention are not limited to use with these particular techniques. Moreover, it will become apparent to those skilled in the art given the teachings herein that numerous modifications can be made to the embodiments shown that are within the scope of the present invention. That is, no limitations with respect to the specific embodiments described herein are intended or should be inferred.

A typical sanitary sewer is an extremely humid, if not condensing, environment. Instruments that are utilized in such an environment are subjected to moisture condensation problems, and are therefore generally protected utilizing protective housings. For example, an exemplary instrument such as that disclosed in U.S. Pat. No. 8,339,584, entitled "Velocity Measuring System," utilizes optical systems for measurement purposes. The optical systems are positioned inside a sealed housing having at least one window. While this sealed housing provides protection and keeps the optics in a clean and dry environment, the outer surface of the window is still sensitive to the harsh sewer environment, and moisture condensation problems occurring on the outer surface of the window may impair the operations of the optical systems enclosed inside.

As disclosed in U.S. Pat. No. 8,339,584, which is incorporated herein by reference, a specially-oriented tube positioned between the window and the sewer environment can be used to isolate and protect the outer window surface from contamination due to solid particle, e.g., falling soil, sewage surcharge or the like. This tube also reduces but does not entirely eliminate the problem of water vapor condensation on the outer surface of the window. As a result, the water droplet condensation on the window can scatter or de-focus (droplets acting like multiple tiny lenses) the optical instruments inside the housing.

One solution for reducing the adverse effects of condensation on the window is to raise the temperature of the window above the dew point of the environment. A simple electrical heater attached to the window can achieve this protection but it requires a significant power budget, which may be too demanding for a galvanic battery at remote, isolated field sites. Therein lies a need for systems and methods to prevent condensation without placing too much demand on a finite power budget.

Embodiments of the present invention are directed to condensation mitigation devices configured to prevent window condensation (and/or fogging) with reduced power consumption. More specifically, using independent measurement parameters and condensation prediction algorithms, a condensation mitigation device in accordance with the present invention is able to predict and/or detect a window condensation event. The condensation mitigation device is powered on only during such an event, and the condensation mitigation device is powered off afterwards to conserve power.

Referring to FIG. 1, a block diagram depicting an apparatus 100 utilized in a humid environment (e.g., in a sewer environment) is shown. As described above, the apparatus 100 may include a protective housing 102 having at least one window 104 to protect the components inside the housing 102. In one embodiment, the components inside the housing 102 include optical devices 106 configured to obtain optical data through the window 104 and a processor 108 (may also be referred to as the controller) configured to process the optical data obtained by the optical devices 106. It is contemplated that an optional tube 116 may be positioned between the window and the sewer environment in certain embodiments to isolate and protect the outer window surface. The inner surface of the tube 116 may be coated with a hydrophilic material that draws moisture away from the optical device. It is also contemplated that the apparatus 100 may include additional components such as batteries, power supplies, data communication modules and the like, which are not explicitly depicted in the figure for simplicity.

In accordance with the present invention, the window 104 is equipped with one or more condensation mitigation devices 118. Such condensation mitigation devices 118 may include, but not limited to, electrical heating elements (also referred to as window heaters), electric actuated wipers, electric actuated mechanical vibrators, electric valve actuated clean air blast jet stream, electric fans or the like, as long as the condensation mitigation devices 118 do not block the optical path(s) of the optical devices 106. For instance, electrical heating elements may be configured as resistive conductors embedded in or placed on the window 104 (e.g., similar to the defoggers used on a rear window of a vehicle). Alternatively, the electrical heating elements may be configured as transparent electrical window heating elements similar to that used on a glass refrigerator door. While certain embodiments in accordance with the present disclosure utilize 2-Watt window heaters, however, it is contemplated that other types of electrical heating elements may also be utilized for heating the window 104. It is contemplated that additional and/or alternative condensation mitigation devices may also be utilized. As previously mentioned, for instance, a mitigation device that provides a short air blast from a compressed air source that clears any residual condensation from the optics, or a mechanical vibrator attached physically to the window to shake off debris and condensation droplets may be utilized without departing from the spirit and scope of the present invention.

In accordance with the present invention, the electrical power cycle of the condensation mitigation device 118 is controlled to reduce power consumption. Various measurement parameters and condensation prediction algorithms are utilized to control the electrical power cycle of the condensation mitigation device 118. The measurement parameters utilized may include, but are not limited to: temperature change parameters, optical signal power loss, scattered light intensity from the window, electrical conductivity of outer window surface or the like, and the condensation prediction algorithms performed based on these parameters will now be described in details.

Figure 2:
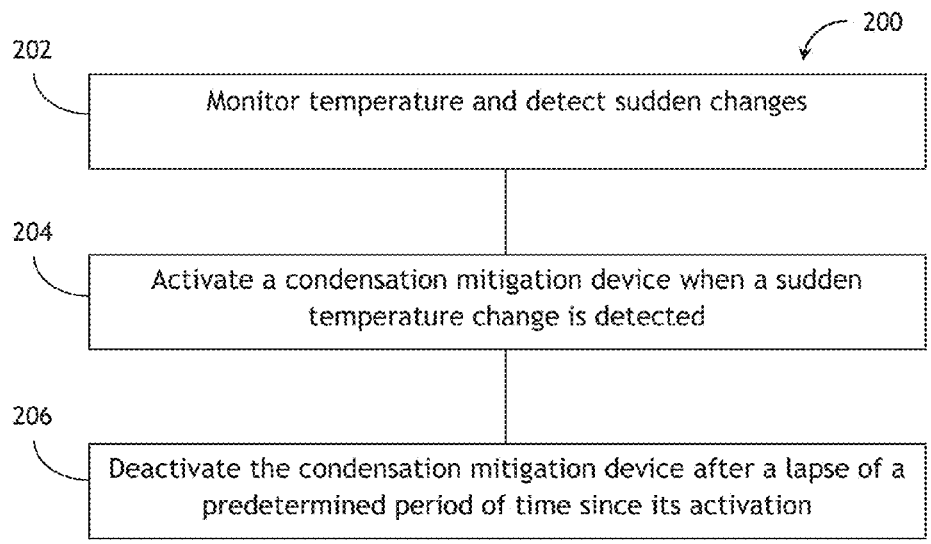
FIG. 2 is a flow diagram depicting a condensation detection method in accordance with an embodiment of the present disclosure.

For instance, it has been observed at sewer sites that a sudden change in the instruments temperature can indicate an occurrence of a window fogging-condensation event. Referring generally to FIGS. 1 and 2, the processor 108 can monitor temperature of the apparatus 100 and detect any sudden changes based upon a threshold derivative value in step 202. It is contemplated that one or more temperature sensors 110 may be utilized to measure the instruments temperature. These temperature sensors 110 may be located at various places inside and/or outside the housing 102 without departing from the spirit and scope of the present disclosure.

Once the processor 108 detects a sudden temperature change based upon a threshold derivative value, the processor 108 powers on the condensation mitigation device 118 in step 204 for a predetermined activation time interval. The processor 108 then powers off the condensation mitigation device 118 in step 206 at the end of the predetermined activation time interval. It is understood that a sudden temperature change refers to a change greater than a threshold value within a short time period. It is also understood that the threshold values, the measurement time period and the activation time interval referenced above may vary according to each particular application site.

Figure 3:
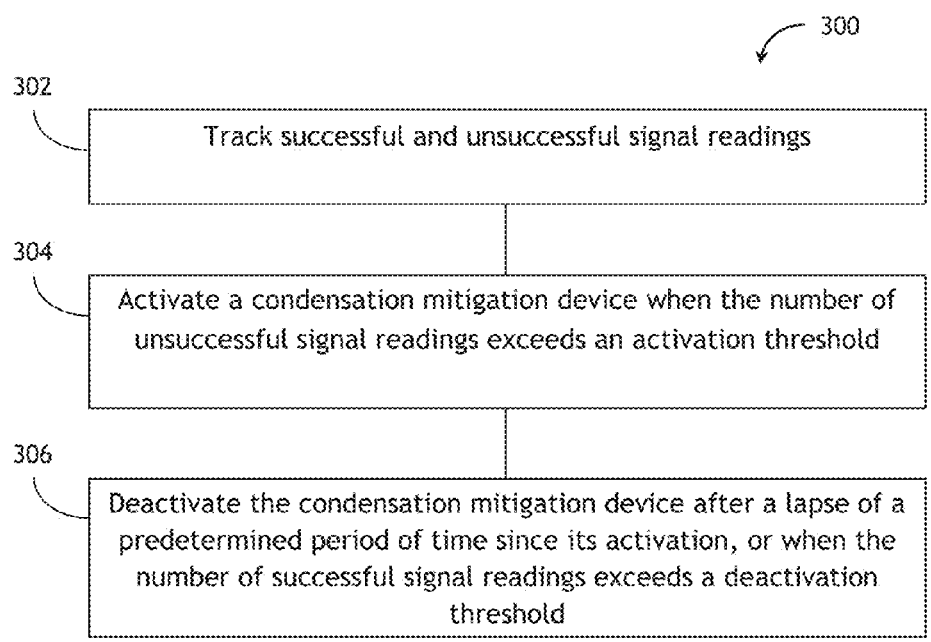
FIG. 3 is a flow diagram depicting a condensation detection method in accordance with an embodiment of the present disclosure.

It has also been observed that a window fogging-condensation event can weaken the signal strength obtained by the optical devices 106 or even cause failures. Therefore, monitoring the signal strength obtained by the optical devices 106 may also help detecting occurrences of window fogging-condensation events. Referring generally to FIGS. 1 and 3, the processor 108 can be configured to monitor the number of errors (e.g., abnormal reading behaviors or failures) and determine whether to activate the condensation mitigation device 118. In one embodiment, the processor 108 keeps track of successful and unsuccessful readings occurring at the optical devices 106 in step 302. Once the number of consecutive failures reaches a predetermined activation threshold, the processor 108 powers on the condensation mitigation device 118 in step 304. The processor 108 may then power off the condensation mitigation device 118 in step 306 at the end of a predetermined time interval, or when the number of consecutive successful readings reaches a predetermined deactivation threshold.

It is noted, however, that since other factors may also cause reading errors, it is possible that the optical devices 106 may fail regardless of whether a window fogging-condensation event is occurring or not. To conserve power, if the optical devices 106 continue to fail after the condensation mitigation device 118 is activated for a sufficient time interval, the condensation mitigation device 118 can be powered off.

It is also noted that in certain applications, the optical devices 106 may be configured to deliver a light beam (e.g., a laser beam as disclosed in the velocity measuring system in U.S. Pat. No. 8,339,584) through the window 104 for measurement purposes. Referring generally to FIG. 1, it has been observed that a fogged window scatters significantly more light than a clear window, and a light sensor 114 (e.g., a photodiode, an imaging device or the like) with supporting circuitry can be utilized to monitor light scattered from the window 104 whenever the light beam is delivered through the window 104.

Figure 4:
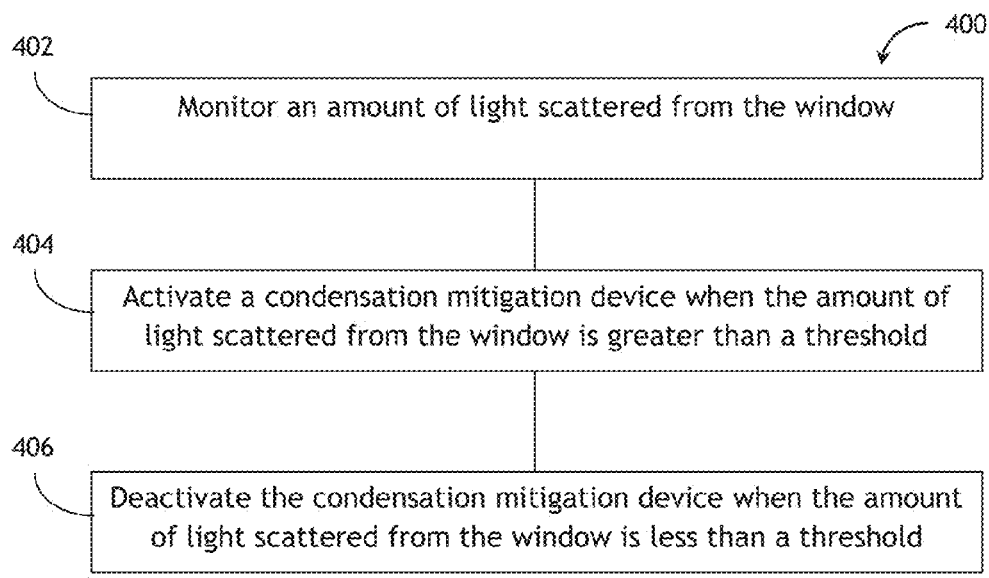
FIG. 4 is a flow diagram depicting a condensation detection method in accordance with an embodiment of the present disclosure.

Referring generally to FIGS. 1 and 4, a light sensor 114 is utilized to monitor light scattered from the window 104 when the optical devices, such as device 106, deliver light beams through the window 104. If the light sensor 114 reading shows a significant increase in scattered light in step 402, the processor 108 powers on the condensation mitigation device 118 in step 404. On the other hand, if the light sensor 114 reading indicates less scattered light, the processor 108 powers off the condensation mitigation device 118 in step 406. In one embodiment, the sensitivity of the light sensor 114 is configured to be high enough to detect an early onset before any significant performance degradation occurs.

Figure 5:
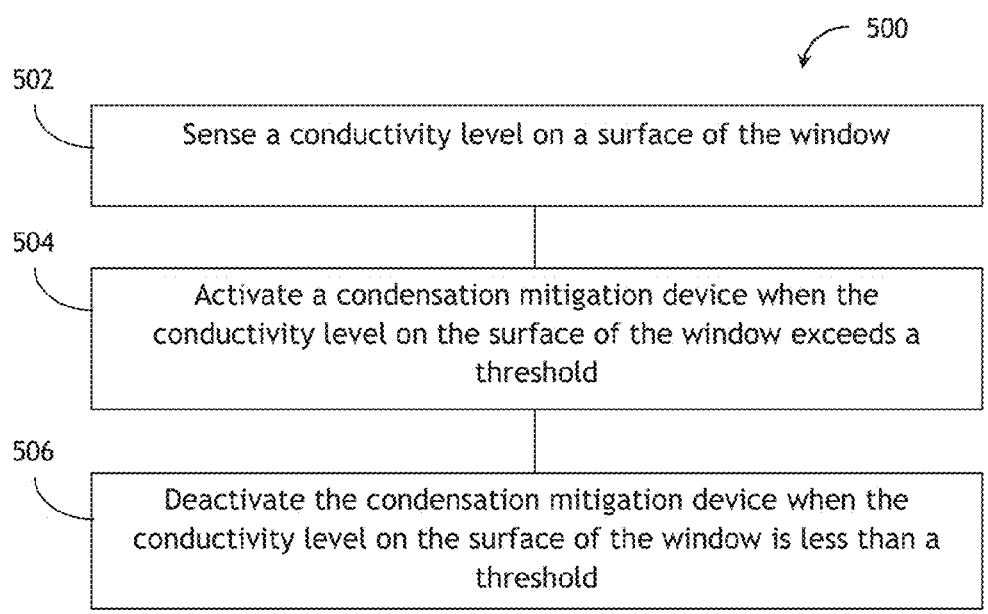
FIG. 5 is a flow diagram depicting a condensation detection method in accordance with an embodiment of the present disclosure.

Furthermore, it is contemplated that conductivity sensors 120 (e.g., electrodes) can be placed on the outer surface of the window 104 and utilized to measure the surface electrical conductivity of the window 104. Since the condensate is water, the conductivity of the outer window surface increases during a window fog-condensation event. Referring generally to FIGS. 1 and 5, in one embodiment, an alternating current (AC) is used to sense the conductivity to reduce electrolysis and associated corrosion at the electrodes. When it is determined that the window surface conductivity rises above a preset threshold value in step 502, the condensation mitigation device 118 is powered on in step 504. When it is determined that the window surface conductivity drops below the preset threshold value, the condensation mitigation device 118 is powered off in step 506.

Figure 6:
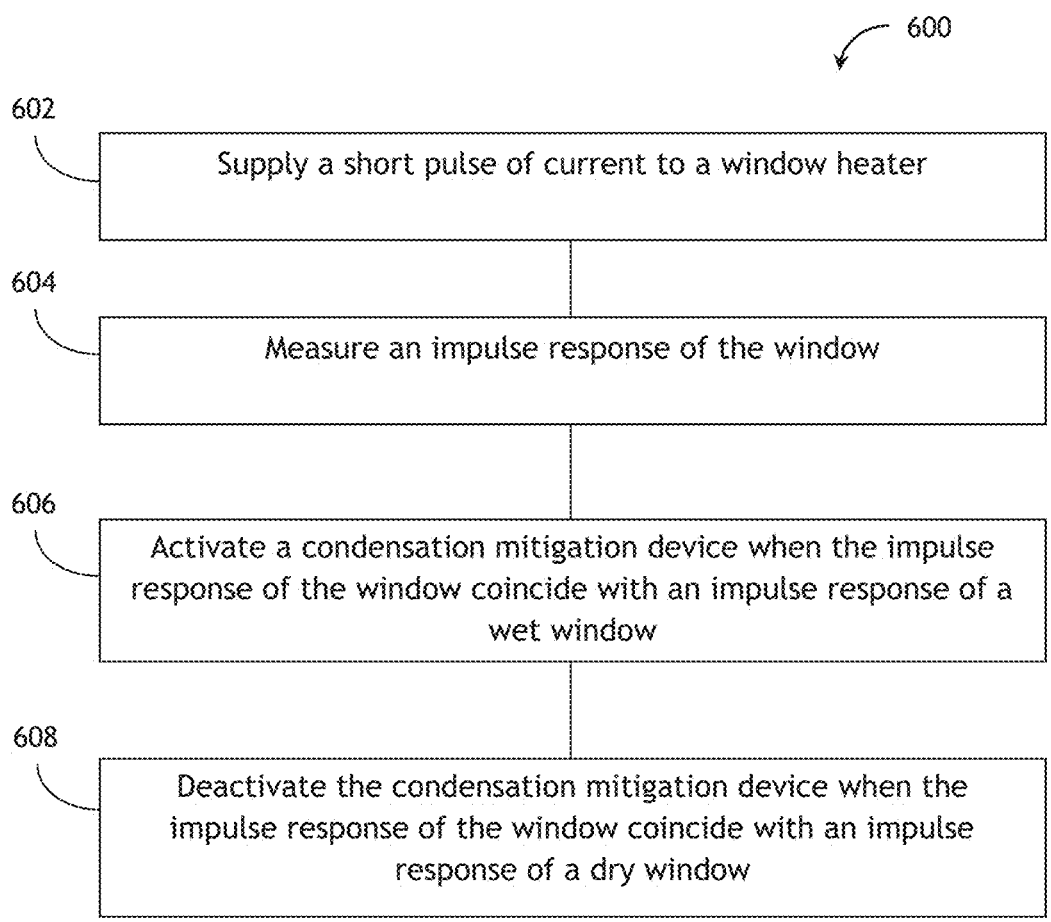
FIG. 6 is a flow diagram depicting a condensation detection method in accordance with an embodiment of the present disclosure.

In addition, it is further contemplated that a small temperature sensor 112 can be mounted on the outer surface of the window 104 and utilized to measure the impulse response of the glass. Referring generally to FIGS. 1 and 6, in one embodiment, a short pulse of current is supplied briefly to a window heater in step 602 and the temperature sensor 112 is used to measure the impulse response of the glass in step 604. This response is expected to be different for wet and dry glass conditions, which may be used to determine whether a window fogging-condensation event is occurring or not and activate/deactivate the winder heater accordingly in steps 606 and 608, respectively. In one embodiment, the temperature sensor 112 is a thermistor, and the thermistor is heated directly by applying the short current pulse and afterwards used to measure the impulse response of the window 104. Using the thermistor as the heating element would be useful to other condensation mitigation mechanisms, other than a main heating element.

It is understood that the measurement parameters and condensation prediction/detection algorithms described above are exemplary. They may operate independently or jointly together in the same system. In addition, principles of the present invention are not limited to the specific apparatus, methods and environments illustratively shown and described above.

It is also understood that while the examples above depict instruments in corrosive and/or humid environments such as sewer environments, the embodiments of the present invention are not limited to the specific apparatus, methods and environments illustratively shown and described above. Embodiments in accordance with the present disclosure are applicable to devices configured for performing noncontact open channel fluid flow measurements as well as various other applications without departing from the spirit and scope of the present disclosure.

Furthermore, while power conservation is critical for battery powered devices, the various condensation prediction/detection algorithms described above are not limited to battery powered devices only. It is contemplated that the condensation prediction/detection algorithms in accordance with the present disclosure is applicable to devices powered by batteries, power mains, hybrid power sources or the like without departing from the spirit and scope of the present disclosure.

It is understood that the present disclosure is not limited to any underlying implementing technology. The present disclosure may be implemented utilizing any combination of software and hardware technology. The present disclosure may be implemented using a variety of technologies without departing from the scope and spirit of the disclosure or without sacrificing all of its material advantages.

It is understood that the specific order or hierarchy of steps in the processes disclosed is an example of exemplary approaches. Based upon design preferences, it is understood that the specific order or hierarchy of steps in the processes may be rearranged while remaining within the scope of the present disclosure. The accompanying method claims present elements of the various steps in a sample order, and are not meant to be limited to the specific order or hierarchy presented.

It is believed that the present disclosure and many of its attendant advantages will be understood by the foregoing description, and it will be apparent that various changes may be made in the form, construction, and arrangement of the components thereof without departing from the scope and spirit of the disclosure or without sacrificing all of its material advantages. The form herein before described being merely an explanatory embodiment thereof, it is the intention of the following claims to encompass and include such changes.

What is claimed is:

1. A condensation detection and mitigation apparatus for a window, the apparatus comprising:
    at least one condensation detection sensor configured for detecting a condensation condition; and
    a controller configured for conditionally activating a condensation mitigation device for the window based on said detection of the condensation condition,
    wherein the at least one condensation detection sensor comprises at least one of:
        an optical sensor configured for detecting a weakened or failed signal reading for a measurement outside of an instrument enclosure returning through the window, wherein the condensation condition is detected when a number of consecutive weakened or failed signal readings is greater than a threshold value; or
        a temperature sensor configured for measuring an impulse response of the window when a short pulse of current is applied to a heating element, wherein the condensation condition is detected based on the measured impulse response of the window.

2. The apparatus of claim 1, wherein the at least one condensation detection sensor further comprises:
    a temperature sensor configured for detecting a temperature change,
    wherein the condensation condition is detected when the temperature changes for more than a threshold value within a predetermined time period.

3. The apparatus of claim 1, wherein the at least one condensation detection sensor comprises the optical sensor.

4. The apparatus of claim 1, wherein the at least one condensation detection sensor further comprises:

an optical sensor configured for monitoring an amount of light scattered from the window,
wherein the condensation condition is detected when the amount of light scattered from the window is greater than a threshold value.

5. The apparatus of claim 1, wherein the at least one condensation detection sensor further comprises:
a conductivity sensor configured for sensing a conductivity level on a surface of the window,
wherein the condensation condition is detected when the conductivity level on the surface of the window is greater than a threshold value.

6. The apparatus of claim 1, wherein the at least one condensation detection sensor comprises the temperature sensor.

7. The apparatus of claim 1, wherein the controller is configured for conditionally activating the condensation mitigation device for the window only for a predetermined period of time upon detection of the condensation condition.

8. The apparatus of claim 1, wherein the at least one condensation detection sensor is further configured for detecting a deactivation condition, and wherein the controller is further configured for conditionally deactivating the condensation mitigation device for the window upon detection of the deactivation condition.

9. The apparatus of claim 1, wherein the condensation mitigation device is battery powered.

10. A condensation detection and mitigation method, comprising:
detecting a condensation condition on a window based on at least one of:
detecting a weakened or failed signal reading for a measurement outside of an instrument enclosure returning through the window, wherein the condensation condition is detected when a number of consecutive weakened or failed signal readings is greater than a threshold value; or
measuring an impulse response of the window when a short pulse of current is applied to a heating element, wherein the condensation condition is detected based on the measured impulse response of the window;
activating a condensation mitigation device for the window based on said detection of the condensation condition; and
deactivating the condensation mitigation device for the window based on at least one of:
a detection of a deactivation condition; and
a lapse of a predetermined period of time since said activation of said condensation mitigation device.

11. The method of claim 10, wherein detecting the condensation condition on the window further comprises:
detecting a temperature change, wherein the condensation condition is detected when the temperature changes for more than a threshold value within a predetermined time period.

12. The method of claim 10, wherein said detecting the condensation condition on the window comprises said detecting the weakened or failed signal reading for the measurement outside of the instrument enclosure returning through the window.

13. The method of claim 10, wherein detecting the condensation condition on the window further comprises:
monitoring an amount of light scattered from the window, wherein the condensation condition is detected when the amount of light scattered from the window is greater than a threshold value.

14. The method of claim 10, wherein detecting the condensation condition on the window further comprises:
sensing a conductivity level on a surface of the window, wherein the condensation condition is detected when the conductivity level on the surface of the window is greater than a threshold value.

15. The method of claim 10, wherein said detecting the condensation condition on the window comprises said measuring the impulse response of the window when the short pulse of current is applied to the heating element.

16. The method of claim 10, wherein the condensation mitigation device is battery powered.

17. A system for performing noncontact open channel fluid flow measurement, comprising:
a protective housing, the protective housing including a window;
an optical device positioned inside the protective housing, the optical device configured for obtaining optical data through the window and performing noncontact open channel fluid flow measurement based on the optical data obtained through the window;
at least one condensation detection sensor, the at least one condensation detection sensor configured for detecting a condensation condition; and
a controller, the controller configured for conditionally activating a condensation mitigation device for the window based on said detection of the condensation condition.

18. The system of claim 17, wherein the protective housing further includes a tube, and wherein an inner surface of the tube is coated with a hydrophilic material that draws moisture away from the optical device.

19. The system of claim 17, wherein the at least one condensation detection sensor further comprises:
a temperature sensor configured for detecting a temperature change,
wherein the condensation condition is detected when the temperature changes for more than a threshold value within a predetermined time period.

20. The system of claim 17, wherein the at least one condensation detection sensor further comprises:
an optical sensor configured for detecting a weakened or failed signal reading for a measurement outside of the protective housing returning through the window,
wherein the condensation condition is detected when a number of consecutive weakened or failed signal readings is greater than a threshold value.

21. The system of claim 17, wherein the at least one condensation detection sensor further comprises:
an optical sensor configured for monitoring an amount of light scattered from the window,
wherein the condensation condition is detected when the amount of light scattered from the window is greater than a threshold value.

22. The system of claim 17, wherein the at least one condensation detection sensor further comprises:
a conductivity sensor configured for sensing a conductivity level on a surface of the window,
wherein the condensation condition is detected when the conductivity level on the surface of the window is greater than a threshold value.

23. The system of claim 17, wherein the at least one condensation detection sensor further comprises:
a temperature sensor configured for measuring an impulse response of the window when a short pulse of current is applied to a heating element, wherein the condensation condition is detected based on the measured impulse response of the window.

24. The system of claim 17, wherein the controller is configured for conditionally activating the condensation mitigation device for the window only for a predetermined period of time upon detection of the condensation condition.

25. The system of claim 17, wherein the at least one condensation detection sensor is further configured for detecting a deactivation condition, and wherein the controller is further configured for conditionally deactivating the condensation mitigation device for the window upon detection of the deactivation condition.

* * * * *